US007824854B2

(12) United States Patent
Arai et al.

(10) Patent No.: US 7,824,854 B2
(45) Date of Patent: Nov. 2, 2010

(54) METHOD OR APPARATUS FOR RECOVERING MICROMATERIAL

(75) Inventors: Fumihito Arai, Aichi (JP); Toshio Fukuda, Aichi (JP); Akihiko Ichikawa, Aichi (JP); Tohoru Katsuragi, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 1029 days.

(21) Appl. No.: 10/508,639

(22) PCT Filed: Jan. 14, 2003

(86) PCT No.: PCT/JP03/00231

§ 371 (c)(1),
(2), (4) Date: Sep. 17, 2004

(87) PCT Pub. No.: WO03/095088

PCT Pub. Date: Nov. 20, 2003

(65) Prior Publication Data
US 2005/0208465 A1 Sep. 22, 2005

(30) Foreign Application Priority Data
May 7, 2002 (JP) .............................. 2002-131656

(51) Int. Cl.
*C12Q 1/68* (2006.01)
*C12M 1/00* (2006.01)
*C12M 1/34* (2006.01)
*C12M 3/00* (2006.01)

(52) U.S. Cl. ..................... 435/6; 435/283.1; 435/287.1; 435/287.9

(58) Field of Classification Search ........................ None
See application file for complete search history.

(56) References Cited

U.S. PATENT DOCUMENTS 4,689,102 A * 8/1987 Prawdzik et al. ............ 156/235

(Continued)

FOREIGN PATENT DOCUMENTS

EP 1 347 353 9/2003

(Continued)

OTHER PUBLICATIONS

Arai et al, Micro Total Analysis Systems 2002, Y. Baba et al (eds.), vol. 2, pp. 928-930 (2002; available to the public on Jan. 1, 2002).*

(Continued)

*Primary Examiner*—Robert T Crow
(74) *Attorney, Agent, or Firm*—Gary C Cohn PLLC (57) ABSTRACT

A substance (for example, methylcellulose) that undergoes a reversible gel to sol phase transition is utilized in a recovery method for specific micromaterials such as DNA molecules, cells, microorganisms and the like, approximately several μm in size, from a mixture containing other micromaterials, and a micromaterial is accurately and conveniently recovered. The present invention is a method of recovering a desired micromaterial in a system comprising a medium that undergoes a reversible phase transition between a sol and a gel, a support material and micromaterials, comprising the steps of converting the medium surrounding the micromaterial to be recovered into a gel locally to immobilize said micromaterial on said support along with the gelled medium, removing the medium and micromaterials not immobilized on said support material and converting the gelled medium to a sol to recover the micromaterial.

19 Claims, 5 Drawing Sheets

U.S. PATENT DOCUMENTS

| | | | | |
|---|---|---|---|---|
| 5,134,070 | A | * | 7/1992 | Casnig ................... 435/173.6 |
| 5,632,957 | A | * | 5/1997 | Heller et al. ............... 422/68.1 |
| 5,959,297 | A | * | 9/1999 | Weinberg et al. ............ 506/12 |
| 6,031,201 | A | * | 2/2000 | Amako et al. .......... 219/121.68 |
| 6,103,528 | A | * | 8/2000 | An et al. .................... 435/395 |
| 6,139,831 | A | * | 10/2000 | Shivashankar et al. ...... 530/351 |
| 6,218,126 | B1 | * | 4/2001 | Yasuda et al. .................. 435/6 |
| 2002/0001813 | A1 | * | 1/2002 | Taylor et al. ................... 435/6 |
| 2003/0104347 | A1 | * | 6/2003 | Mori et al. ................... 435/1.1 |
| 2004/0050436 | A1 | | 3/2004 | Tsukita et al. |

FOREIGN PATENT DOCUMENTS

| | | |
|---|---|---|
| JP | 6-273382 | 9/1994 |
| JP | 6-343451 | 12/1994 |
| JP | 8-9966 | 1/1996 |
| JP | 11-210750 | 8/1999 |
| JP | 11-346756 | 12/1999 |
| JP | 2001-095558 | 4/2001 |
| JP | 2001-145478 | 5/2001 |
| JP | 2003-102465 | 4/2003 |
| WO | WO 02/44823 | 6/2002 |

OTHER PUBLICATIONS

Belov et al, PLOS Biology, vol. 4, pp. 0317-0328 (2006).*
Aria et al, Micro Total Analysis Systems 2002, Y. Baba et al (eds.), vol. 2, pp. 548-550; reference obtained from the Library of Congress.*

* cited by examiner

METHOD OR APPARATUS FOR RECOVERING MICROMATERIAL

This application is a national stage entry of PCT/JP03/00231, filed 14 Jan. 2003, which claims priority to Japanese Application Serial Number JP 2002-131656, filed 7 May 2002.

TECHNICAL FIELD

The present invention relates to a method to recover a specific micromaterial from among numerous micromaterials and a device thereof, more specifically, to a method to recover specific micromaterials such as DNA molecules, cells, microorganisms and the like from among other micromaterials present.

PRIOR ART

The conventional methods to recover specific micromaterials such as DNA molecules, cells, microorganisms and the like from other micromaterials present includes the removal of a target material from Petri dishes using micropipettes while observing the material under an optical microscope and the use of cell sorters [Nihon Kikai Gakkai Ronbunshu, Vol 67, Edition c, pp. 146-153 (January 2001), Electrophoresis 2001, 22, 283-288]. However, the method using micropipettes requires skilled techniques select, sort and recover high purity micro samples microscopically, and also requires enormous time and expense to implement the practice. While the method using cell sorters proved to be effective on target materials that are several tens of microns in size but were difficult to apply to microorganisms several micrometers in size. Cell sorters also involved sequential separation work on samples lined up in a row and could not be used to quickly remove optionally selected targets from randomly dispersed samples.

The inventors has proposed a high throughput separation system utilizing a non-contact type manipulation wherein a separation is executed using a combination of laser traps, electrophoresis and microcapillary flow in a micro fluid circuit (Japanese Publication of Unexamined Patent Applications Hei 11-346756, Hei 11-210750, 2001-095558 and 2001-145478). However, microorganisms were transported using a direct laser trap, and the procedure was accompanied by the risk of microbial damage. An indirect transfer method was also proposed to avoid the damage wherein a microtool would be used to assist a laser trap by pushing or pulling microorganisms. However, complicated operations presented problems in actual applications.

PROBLEMS FOR THE INVENTION TO SOLVE

The present invention is a method to recover specific micromaterials such as DNA molecules, cells, microorganisms and the like from other micromaterials present, and the objective of the present invention is to provide a method that can solve the problems mentioned below.

1. Desired samples are selected from a large amount of randomly dispersed samples while examining them using optical microscope. Commonly used cell sorters cannot achieve this mission.
2. Desired samples are selected from randomly dispersed samples. The method should remove only necessary samples when needed.
3. High throughput separations are made possible.
4. Several samples are selected from a large number of samples (for example, 50,000 samples) easily and accurately.
5. Direct irradiation of separation targets by laser is avoided, and damage to the separated material is prevented. This issue is particularly important for microbial separations since microorganisms are sometime decimated due to temperature increases or ultraviolet radiation when directly exposed to laser light.
6. The selection process is automated by combining fluorescence observation and image processing. When conducting fluorescence observation, the background noise generated causes problems such as a decline in image resolution and blurred images. The merits of this approach includes an extensive reduction in background noise levels, the possibility of high contrast examinations and there being no need for attaching expensive optical systems such as proximity fields when unnecessary materials that cause noise can be removed.
7. This system can be combined with microbial culture chips allowing further integration to occur to execute the steps from separation to culturing on one chip.

MEANS TO SOLVE THE PROBLEMS

The present invention focuses on the utilization of a substance that causes a reversible phase transition between a sol and a gel as a medium for the recovery of only a target micromaterial from a solution containing numerous micromaterials such as cells, microorganisms and DNA molecules and completes an accurate and yet simple recovery method upon developing a simple method to induce the phase transition.

In the method of the present invention, either a substance that undergoes a reversible phase transition between a gel and a sol in which numerous micromaterials are dispersed or a solution containing the substance is allowed to flow into a microchannel. The micromaterials present in a specific observation zone are, for example, examined and selected microscopically. Target micromaterials are selected, particularly those present in the vicinity of a support material (the vessel bottom surface and the like), and the surrounding area is locally gelled along with the target material to immobilize the target material on the support material (the vessel bottom surface and the like). After the target material is immobilized on the support material, the flow inside the microchannel is activated, and those micromaterials not immobilized are removed. After thorough removal, the medium is converted into a sol to lower the viscosity. The target material can be recovered by re-establishing a flow.

That is, the present invention is a method of recovering a desired micromaterial in a system comprising a medium that undergoes a reversible phase transition between a sol and a gel, a support material and micromaterials, comprising the steps of converting the medium surrounding the micromaterial to be recovered into a gel locally to immobilize said micromaterial on said support along with the gelled medium, removing the medium and micromaterials not immobilized on said support material and converting the gelled medium to a sol to recover the micromaterial. The micromaterial contains micromaterial(s) desired for recovery and unnecessary micromaterials, and the present invention makes possible highly accurate recovery of only the desired micromaterial from the mixture.

Any medium can be used in the method of the present invention provided that it can undergo a reversible sol to gel phase transition. Of such media, those that can induce such a phase transition due to temperature changes are particularly convenient to use. That is, this medium has a sol to gel phase transition temperature, forms a gel when heated to at or above said phase transition temperature and forms a sol when cooled to at or below said phase transition temperature. The phase transition temperature is preferably room temperature to 90° C., more preferably 20 to 85° C., even more preferably 30 to 60° C., although it depends on the properties of the target micromaterials in the present invention. For separation and recovery of a microorganism, this phase transition temperature is particularly preferably 30 to 50° C. In this case, a water soluble cellulose derivative or a solution thereof is preferred as the medium, and methylcellulose is more preferred as the cellulose derivative. For example, Metolose SM, SH, SE and the like, manufactured by Shin-Etsu Kagaku Kogyo K.K., can be mentioned. Furthermore, a polymer of poly-N-isopropyl acrylamide and a poly(ethylene glycol) derivative may be used as the medium. This polymer is commercially available as Mebiol Gel (registered trade mark, Ikeda Rika K.K., transition temperature 22° C.), for example, but the transition temperature can be modified to set at 30° C. to 32° C. through molecular design.

For example, methylcellulose (Metolose ) ordinarily is transformed into a turbid white gel when its 2% solution is heated to about 55° C. and is converted into sol again when cooled. The transition is reversible with temperature change, and methylcellulose is nontoxic to biological matter and to humans since it is a fiber. Furthermore, the gel formation temperature is lowered by adding NaCl, NaOH and the like. For example, the gel formation temperature can be lowered to about 40° C. when 5% NaCl is added to this 2% solution.

Figure 1:
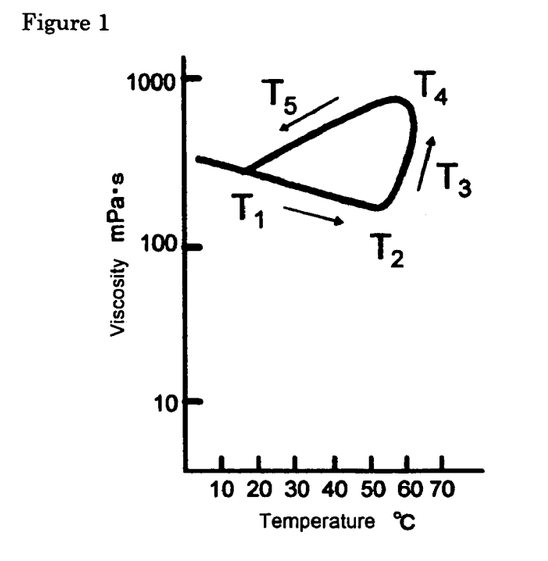
FIG. 1 is a graph showing viscosity changes as function of methyl cellulose (Metolose SM) temperature. This graph exhibits hysteresis property.

Methylcellulose (Metolose SM) exhibits hysteresis properties with the temperature induced viscosity changes as shown in FIG. 1. Therefore, multiple numbers of targets may be removed by utilizing this property. The flow scheme is shown below.

Figure 2:
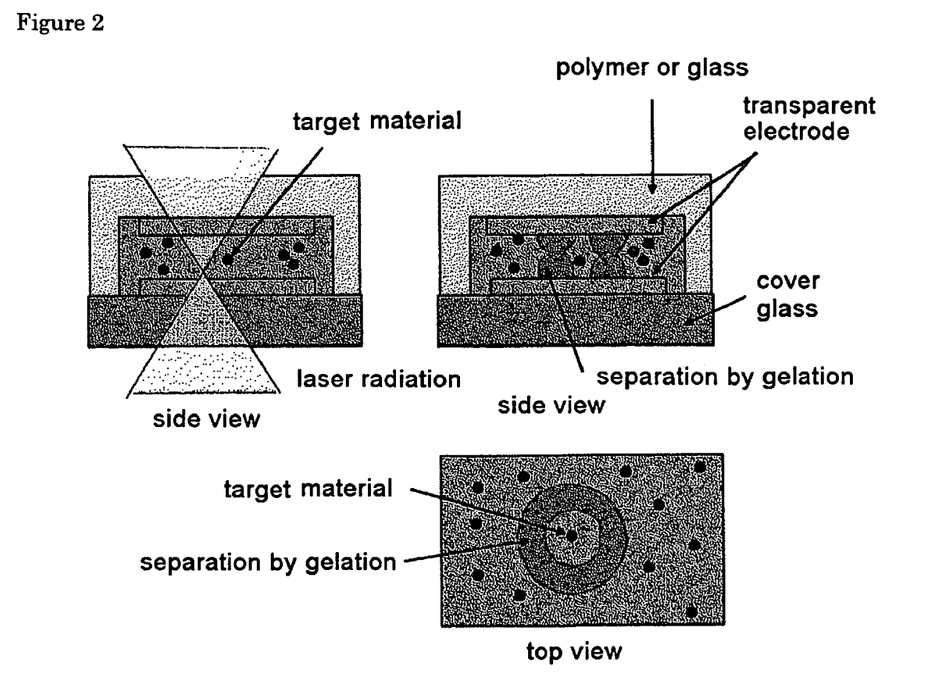
FIG. 2 shows a method to immobilize a target material by locally heating the area surrounding the target material.

1. An electrode is used to heat the solution to T2, a temperature just below the gel formation initiation temperature. At this point, the entire solution is in the form of a sol.
2. A solution containing a mixed sample of microorganisms, cells or DNA materials is allowed to flow.
3. A laser is used to heat only the area surrounding the target to T4, a temperature exceeding the gel formation initiation temperature to form a gel. The laser is immediately discontinued after the heating. However, the area surrounding the target remains gelled since the temperature once exceeded T4, the gel formation temperature, and remains supported by the bottom surface. The area surrounding a target material may be heated locally without heating the target material itself and the target material may be immobilized on a support material, when direct laser irradiation and direct target material heating using other heating means are not appropriate. An example is shown in FIG. 2.
4. By repeating step 3, multiple numbers of targets can be maintained over a heating electrode. When microorganisms and cells are targets, the heating electrode may be covered with an insulator in order to avoid killing microorganisms and cells by electricity.
5. A cleaning flow is generated to remove the non-target material. The target is fixed on the bottom surface at this point due to the gelled areas and is not moved by the flow. Therefore, only the non-target material is removed.
6. Steps 2-5 are repeated, and optional numbers of target materials can be retained.
7. The temperature reaches T1 instantaneously when the heating electrode is turned off, and the gelled areas surrounding a target are instantaneously converted into a sol that can move with the flow without adhering to the bottom surface.
8. The recovery flow is allowed to move, and the target material is recovered from a recovery port.

In the examples described later, the hysteresis properties are advantageously utilized and multiple numbers of samples can be extracted on one electrode.

The support material is used to immobilize a target material and to immobilize the target material when removing unnecessary materials. Therefore, the support material is not particularly restricted as long as it conforms to such objective. A support material is ordinarily a vessel used to contain micromaterials and a medium, but, in addition to the vessel, a support material shaped like rods, boards, screen or grating may also be used. The material of construction for the support material is not particularly restricted. However, a transparent support material is preferred since the transparency makes it possible to shine light through the support material, the target material can be observed and a type of microscope for observation using transmission lighting methods can be utilized. A medium that can be heated is more convenient when the sol to gel phase transition is induced by changing the temperature. For example, a support material that is a transparent electrode (ITO) is particularly preferred since it can be irradiated with infrared laser light to induce localized heating and it can also heat the entire material or a portion of it by allowing electrical current to pass.

Any micromaterial that can be incorporated into a gelled medium may be used as a target for a method of the present invention, and target material sizes from several nm to about 200 μm, preferably several nm to about 30 μm are particularly suitable. The method of the present invention is particularly suited for separation and recovery of micromaterials such as DNA molecules, cells, microorganisms and the like. Such micromaterials can ordinarily be identified visually unaided or microscopically for sample shape, size, color, fluorescence reaction and the like. The micromaterials may also be identified when the micromaterials have some markers. In the present invention, such selection does not necessarily have to be conducted visually and may be conducted automatically using an automatic identification device using a CCD camera or a device that automatically senses fluorescent reactions.

Background noise is considered a problem when examining a micromaterial such as DNA and the like. However, the background noise problem can be resolved by using thermal gelation as in the present invention, immobilizing only the DNA near the cover glass and reversing the thermal gelation for the observation after removing the DNA floating on top.

Figure 3:
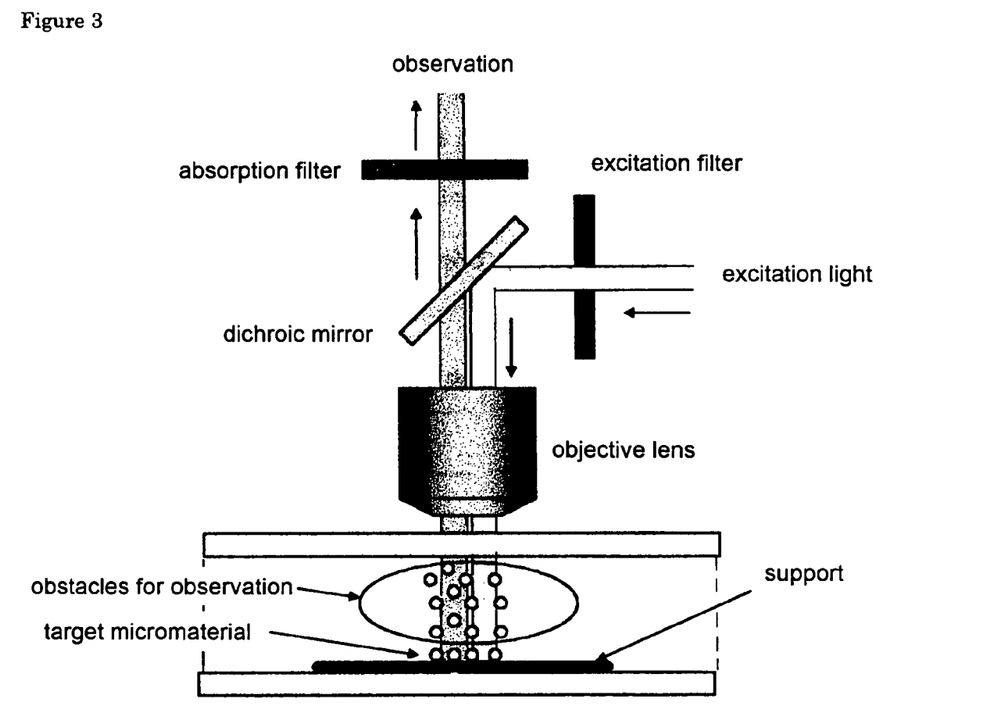
FIG. 3 shows an observation method after temporarily immobilizing only the micromaterials near a support material using a method (thermal gelation) of the present invention.

A conventional method utilizing evanescent illumination (for example, using TIRFM, a fully reflective fluorescent microscope system manufactured by Olympus Kogaku Kogyo) uses evanescent light for the excitation and induces only the fluorescent molecules in close proximity of the glass to emit light. However, the use of evanescent illumination required the involvement of an expensive optic system. The use of a method (thermal gelation) of the present invention temporarily immobilizes only the micromaterials near the support material shown in FIG. 3 and can remove the fluorescent molecules that cause observation noise and obstacles through cleaning. Therefore, a highly sensitive observation (low background noise) is made possible using fluorescent microscopes that are most commonly utilized.

Background noise generally interferes with drop light fluorescent observations using mercury lamps, but the approach can be applied to the observation of various samples other than DNA by utilizing a method of the present invention to dye with a fluorescent substance only that part of a sample desired for observation.

The means through which a gel and sol phase transition is induced reversibly in the present invention may be appropriately selected according to the nature of the substance used to induce a reversible gel and sol phase transition. However, the use of a substance that undergoes a reversible gel to sol phase transition using temperature is convenient. The localized heating method employed is not particularly restricted. A microelectrode may be manufactured using microtooling methods and may be locally heated using resistance wire heating or an infrared irradiation device.

The use of resistance wire heating to heat an electrode when the target material is a microorganism requires planning to prevent killing the microorganisms with the electric current, and covering the resistance wire with an insulator is desirable. As the insulator, silicon oxide, silicon nitride, polyimide resin and the like may be mentioned.

Heating a medium to a temperature above the phase transition temperature by applying infrared radiation and cooling the medium to a temperature below the phase transition temperature by terminating the radiation is particularly preferred as the localized heating method. A conventional infrared irradiation device may be used, but the use of an infrared laser is preferred. A laser may be used to irradiate a target material as is or a lens and the like may be used to focus the light on a target material for the irradiation. A YAG laser (Nd-YAG laser), an Nd:YVO$_4$ laser, a CO$_2$ laser, a ruby laser and the like may be used as the infrared laser, but the use of a YAG laser or Nd:YVO$_4$ laser is convenient.

Hot water may be poured into an addition port as a heating method. In addition, the present invention is a device for recovering micromaterials comprising a space to retain a medium that undergoes a reversible phase transition between a sol and a gel by changing temperature and a support material, means to heat said support material to a temperature of at least the phase transition temperature of said medium, means to heat said support material locally to a temperature of at least the phase transition temperature of said medium, a flow channel through which said medium is added to said space, a flow channel through which a cleaning fluid is added to said space, a flow channel through which the cleaning fluid is discharged from said space and a flow channel through which said medium is discharged from said space. Any one of these flow channels may also function as other flow channels.

This device may also be appropriately further provided with heating means such as an infrared irradiation device to irradiate the aforementioned space, but an infrared laser is preferred and a YAG laser or an Nd:YVO$_4$ laser is more preferred. Furthermore, the device may also be equipped with a lens designed to concentrate the infrared rays from an infrared irradiation device into the aforementioned space. In addition, this device may also be equipped with a microscope to observe the aforementioned space. This device, furthermore, may also be equipped with a shape identification device utilizing, for example, a CCD camera and a device that automatically senses fluorescent reactions to automate the identification process.

EFFECT OF THE INVENTION

Conventional cell sorters separate cells by inducing serial flows, but the present invention can select randomly dispersed target materials by two dimensionally spreading a sample and comparing the properties. By expanding the observation zone, 10,000 to 40,000 micromaterials can be compared and sorted in a single pass using this method, accelerating the separation speed. In addition, a selected target material can be attached to the interior of a microchip or a micromanipulator or retained inside a suctioned pipette chip making high speed recovery simple to execute when necessary.

The present invention is illustrated using the examples shown below, but the examples are not intended to limit the present invention.

EXAMPLE 1

Figure 4:
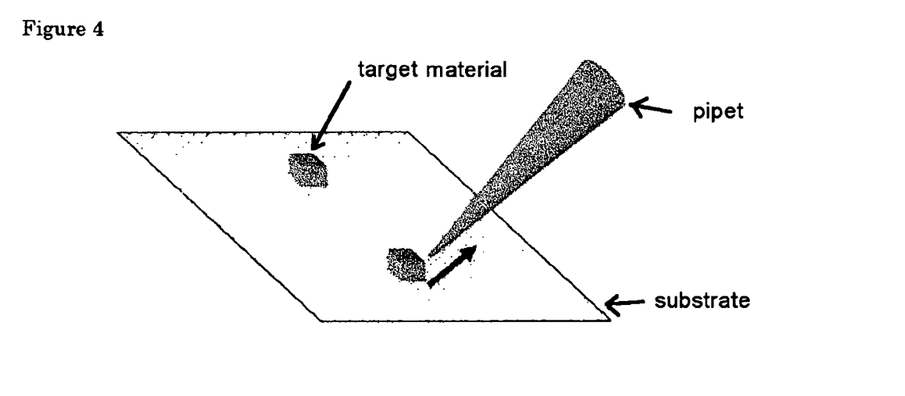
FIG. 4 shows a recovery mode using a pipette after a target material is immobilized using a gel.

In the present example, a target material is immobilized by a gel and is recovered using a pipette. The execution mode of the process is shown in FIG. 4.

A mixture of 0.01 g of yeast (particle size: about 6 μm) and 8 ml of a 2% aqueous solution of methylcellulose (Shin-Etsu Kagaku Kogyo K.K., Metolose SM-4000) was spread flat on a substrate (a glass with an electrode (ITO) film formed on the surface) using spin coating.

By using this type of transparent substrate, a target material can be observed using an inverted microscope. This substrate was examined using an inverted optical microscope (Olympus Co., IX70), and a target material was selected. A particular target was selected from the materials present near the bottom, and the substrate in the vicinity of the target material was irradiated by concentrating an Nd:YVO$_4$ laser (Spectra-Physics Co., J20-IR-2E, wavelength: 1064 nm) through an objective lens (Olympus Co., UPlanApo 100×/1.35). This irradiation locally heated the area surrounding this substrate by the laser, and the target material was immobilized on the substrate since methylcellulose was gelled along with the target material. The gel formed by the laser irradiation remained in a gel state for a certain duration of time, therefore multiple numbers of target materials were immobilized at this point.

After immobilizing the target materials with the gel, water was used to wash and remove other unnecessary materials. After the unnecessary materials were sufficiently removed, the target material heating was discontinued to convert the target material into a sol and release it from immobilization. The target material was recovered using a recovery pipette attached to a micromanipulator.

EXAMPLE 2

Figure 5:
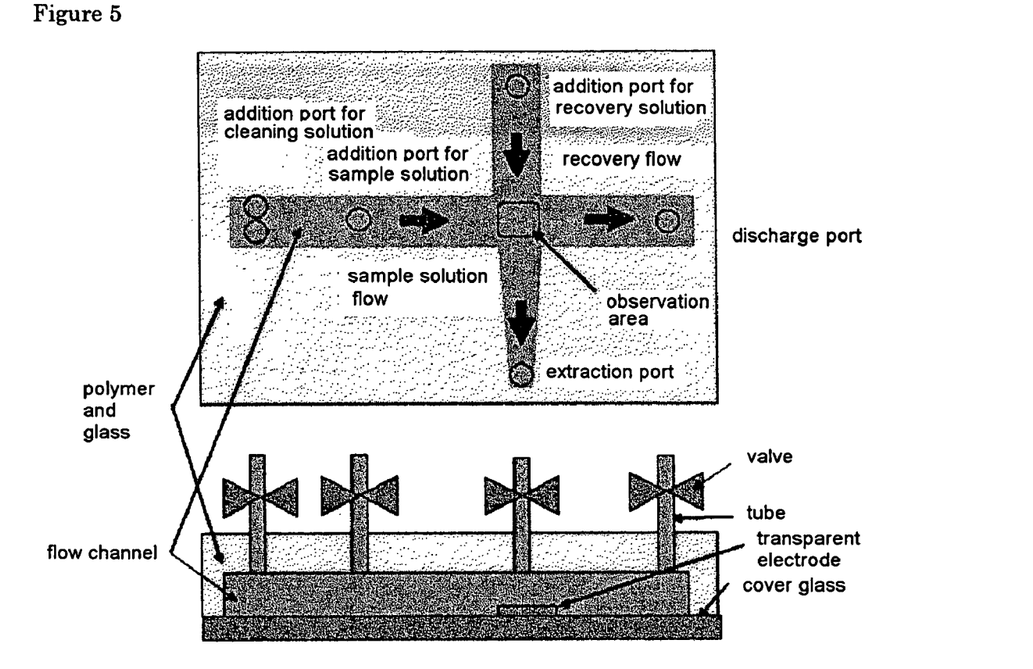
FIG. 5 is a microchip schematic diagram. The top figure is a view of the microchip from above, and the lower figure is a cross sectional view.
Figure 6:
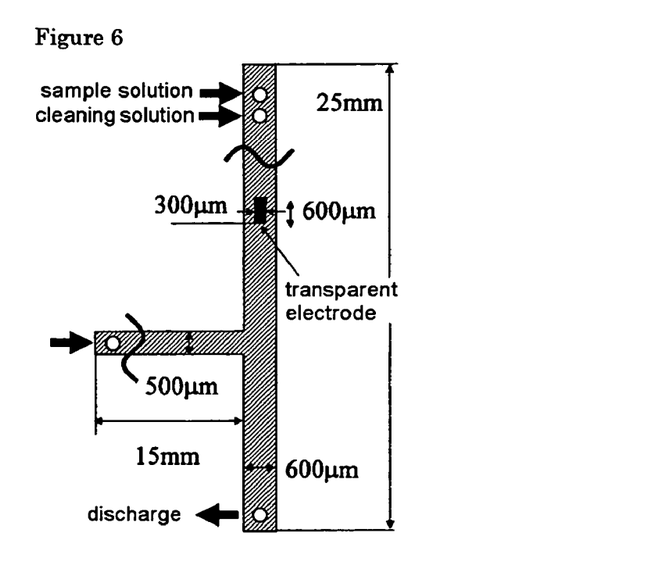
FIG. 6 is a schematic diagram of another microchip. The microchip was viewed from above.

Schematic diagrams of the microchips used in the present examples are shown in FIGS. 5 and 6.

These microchips are equipped with two intersecting flow channels. The form for these two flow channels were created using microtooling, and the microfluid chips were shaped from PDMS (polydimethylsiloxane). The two flow channels intersected forming a cross in the microchip shown in FIG. 5, and the two flow channels intersected forming a T in the microchip shown in FIG. 6. A single discharge port functioned to discharge both a sample and a cleaning solution.

One flow channel was used to add a sol/gel phase transition substance containing a target material and to move water used to clean unnecessary materials other than subsequently fixed target materials. The other flow channel was used to recover the fixed target material.

The intersection of the two flow channels (an observation zone) was observed using an inverted optical microscope (Olympus Co., IX70), and the zone was irradiated by focusing an Nd:YVO$_4$ laser (Spectra-Physics Co., J20-IR-2E, wavelength: 1064 nm) through an objective lens (Olympus Co., UPlanApo 100×/1.35). A transparent electrode (Matsunami Glass Kogyo K.K., a thin glass sheet with ITO) was formed as a film in the bottom of the observation zone, and a pattern was created. Furthermore, the surface of this transparent electrode was coated using silicon oxide.

This microchip was positioned on the stage of an optical microscope. The stage was movable, and the microchip could be observed using microscope and irradiated using a laser while moving the observation zone.

A mixture of 0.01 g of yeast (particle size: about 6 µm) and 8 ml of a 2% aqueous solution of methylcellulose (Shin-Etsu Kagaku Kogyo K.K., Metolose SM) was added from the addition port of this microchip. The valve in the extraction port was then closed at this point.

An electrical current was allowed to flow through the transparent electrode to warm it, and a gel was formed on the transparent electrode surface to temporarily immobilize the sample and impurities present near the surface. Water was subsequently added from a cleaning water addition port, and the methylcellulose that was not immobilized was removed.

Figure 7:
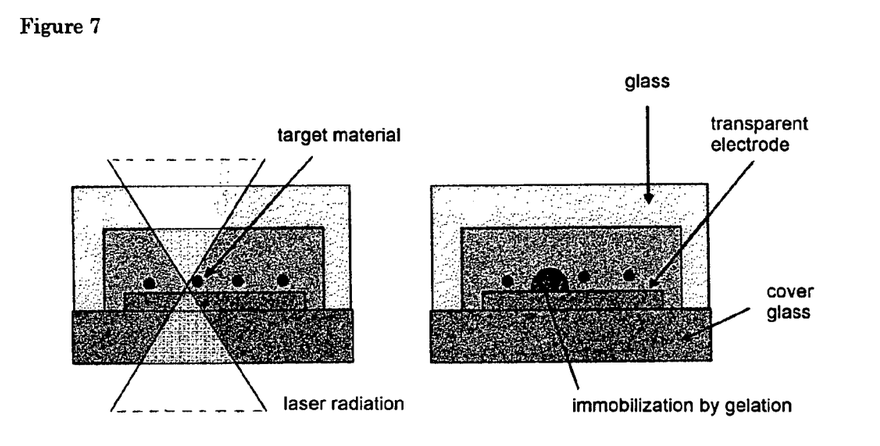
FIG. 7 shows the concentration of a laser light on a transparent electrode in Example 2 (figure on the left) and the gelation mode of methylcellulose incorporating a target material (figure on the right).

The cooled transparent electrode was subsequently warmed to near the thermal gelation initiation temperature but not exceeding it by passing an electrical current, and the vicinity of where two of the microflow channels intersected was observed using an inverted microscope to select a target material. After selecting a target material, the transparent electrode in the vicinity of the target material (the aforementioned sample) was irradiated with the focused laser. The transparent electrode in the area exposed was heated, and the methylcellulose in the area was gelled while entrapping the target material. The design is shown in FIG. 7. Cleaning water was subsequently added from a cleaning water addition port, and methylcellulose and other unnecessary materials not immobilized were removed and discharged through a discharge port.

The valve on the discharge port was subsequently closed, and a solution containing a sample was added from the addition port. By repeating similar procedures, the necessary quantity of the target material was recovered. The purity of the recovered material obtained using the device shown in FIG. 6 was better than that obtained using the device shown in FIG. 5 since the residence time of cleaning and recovery solutions was shorter.

EXAMPLE 3

A microchip similar to the one described in Example 1 with the exception of having transparent electrodes (ITO) located in top and lower sections of an observation zone was used.

A mixture of a sample and methylcellulose similar to the one described in Example 1 was added to this microchip.

Figure 8:
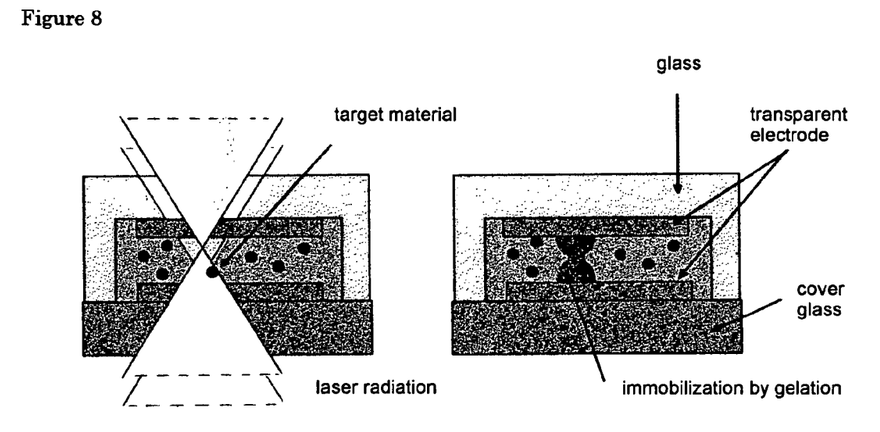
FIG. 8 shows the concentration of a laser on a transparent electrode in Example 3 (figure on the left) and the gelation mode of methylcellulose incorporating a target material (figure on the right).

Both transparent electrodes were warmed by passing electrical current, and the sample and impurities were entirely immobilized once. The target material vicinity was subsequently irradiated using a laser in the same manner as described in Example 1. The design is shown in FIG. 8. The power to the transparent electrodes was subsequently terminated, and water was added from a cleaning water addition port to remove unnecessary materials. The target material remaining was subsequently recovered.

One merit of the current method is that a sample not near the bottom surface can be immobilized in the environment since the immobilization occurs through localized heating using bottom and top electrodes.

EXAMPLE 4

Figure 9:
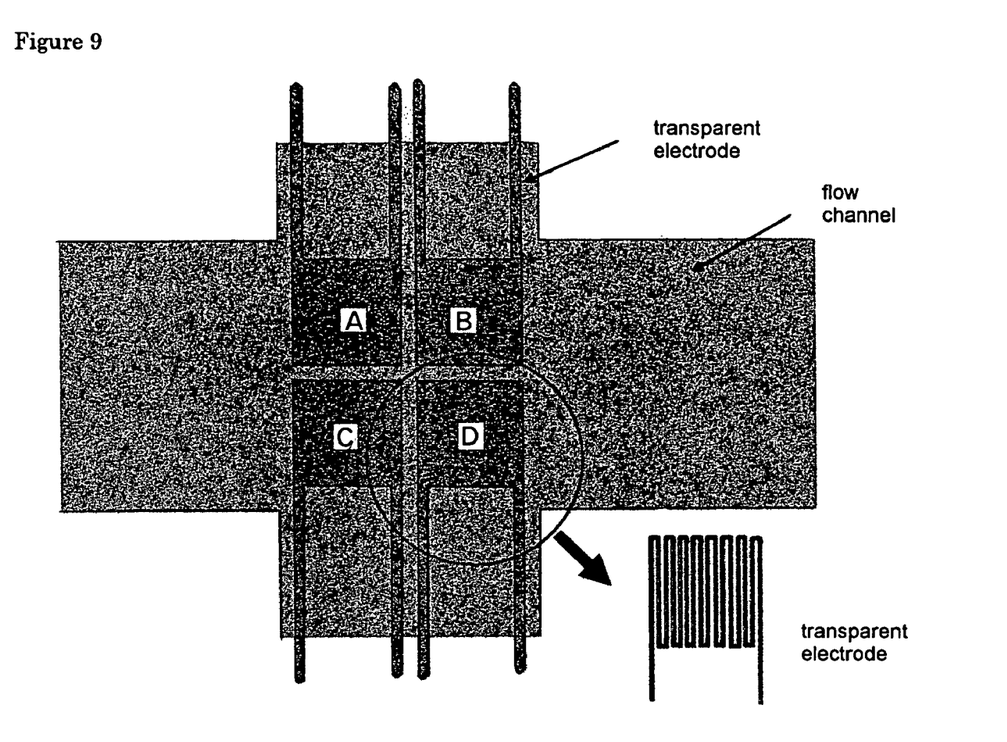
FIG. 9 is a microchip schematic diagram. A-D represent heatable electrodes. The vertical and horizontal flow channels are the same as those shown in FIG. 7.

In the present example, a target material was immobilized by heating that combined electrical overheating of an electrode with localized heating using laser irradiation. A schematic diagram of this microchip is shown in FIG. 9.

This microchip was positioned on a microscope stage. The observation zone could be changed according to the observation magnification of the microscope, and a broad area could be observed by moving the stage. A large amount of sample can be treated by preparing multiple numbers of electrodes, and the work efficiency can be improved. In order to realize immobilization through electrical overheating of an electrode, only one target material of about several microns can be immobilized and, therefore, the number of electrodes needed to be increased. Many electrodes are needed to remove only one target material from several thousands to several tens of thousands of micromaterial samples, and the system could become complex. Therefore, multiple numbers of electrodes that can immobilize several thousands to several tens of thousand of micromaterial samples at once were prepared. In the present example, electrodes A-D, four independent electrodes, were prepared.

The sample from Example 1 was used, appropriate valves were controlled for sample additions, and cleaning and recovery were as in Example 1.

A micromaterial sample was first added, and electrical current was passed through all electrodes to heat them to immobilize the micromaterial sample. Cleaning water was allowed to flow as needed, and the samples that were not immobilized were washed away. Next, the flow of electricity and the heating of Electrode (A) were terminated, and a target material was decided upon examining the micromaterial sample on Electrode (A). The target material was immobilized through laser irradiation and localized heating. After the immobilization, materials other than the target material in the vicinity of Electrode (A) were washed away using a flow of cleaning water. Electrode (A) was subsequently heated using a flow of electrical current, and the target material previously selected was immobilized before laser irradiation was terminated. Next, the micromaterial sample on Electrode (B) was examined, and the same process described above was repeated. Similar procedures were repeated for Electrodes (C) and (D), and at least four target materials were immobilized. Finally, electrical flow and heating were terminated only for the electrode containing a desired target material after washing, and only the target material was extracted using a recovery flow.

An example involving four electrodes is described here, but a large amount of sample can be processed rapidly when the number of electrodes involved is increased. The separation process can be automated by automating the stage of the microscope.

The invention claimed is:

1. A method of recovering a desired micromaterial from a mixture of micromaterials: comprising: providing a system comprising a medium that undergoes a reversible phase transition between a sol and a gel, a support material and a mixture of micromaterials, converting a portion of the medium surrounding the desired micromaterial into a gel locally to immobilize said desired micromaterial on said support material along with the gelled portion of the medium, removing the medium and micromaterials that are not immobilized on said support material, and converting the gelled medium to a sol to recover the desired micromaterial.

2. The method as in claim 1 wherein the medium has a sol to gel phase transition temperature, forms a gel when heated to at or above said phase transition temperature and forms a sol when cooled to at or below said phase transition temperature.

3. The method as in claim 2 wherein the phase transition temperature is from room temperature to 90° C.

4. The method as in claim 2 wherein the medium is a water soluble cellulose derivative or a solution thereof.

5. The method as in claim 4 wherein the cellulose derivative is methylcellulose.

6. The method as in claim 1 wherein the support material is transparent.

7. The method as in claim 6 wherein the support material is a transparent electrode.

8. The method as in claim 1 wherein the desired micromaterial has a marker for identification.

9. The method as in claim 1 wherein the desired micromaterial is a DNA molecule, a cell or a microorganism.

10. The method as in claim 2 wherein the medium is heated to a temperature at or above the phase transition temperature by applying infrared irradiation and the medium is cooled to a temperature at or below the phase transition temperature by terminating the infrared irradiation.

11. The method as in claim 10 wherein the medium is heated using an infrared laser.

12. The method as in claim 11 wherein the infrared laser is a YAG laser or an Nd:$YVO_4$ laser.

13. The method as in claim 3 wherein the medium is a water soluble cellulose derivative or a solution thereof.

14. The method as in claim 3 wherein the support material is transparent.

15. The method as in claim 2 wherein the desired micromaterial has a marker for identification.

16. The method as in claim 15 wherein the medium is heated to a temperature at or above the phase transition temperature by applying infrared irradiation and the medium is cooled to a temperature at or below the phase transition temperature by terminating the infrared irradiation.

17. The method as in claim 2 wherein the desired micromaterial is a DNA molecule, a cell or a microorganism.

18. The method as in claim 17 wherein the medium is heated to a temperature at or above the phase transition temperature by applying infrared irradiation and the medium is cooled to a temperature at or below the phase transition temperature by terminating the infrared irradiation.

19. A method of recovering a target micromaterial from a mixture of micromaterials, comprising providing a system comprising a medium that undergoes a reversible phase transition between a sol and a gel, a support material and a mixture of micromaterials, forming the medium into a sol which contains a mixture of micromaterials, examining the sol to identify and select at least one target micromaterial, converting a portion of the medium surrounding the target micromaterial into a gel locally to immobilize said target micromaterial on said support material along with the gelled portion of the medium, removing the medium and micromaterials that are not immobilized on said support material and converting the gelled medium to a sol to recover the target micromaterial.

* * * * *